United States Patent [19]
de la Fuente

[11] Patent Number: 5,306,258
[45] Date of Patent: Apr. 26, 1994

[54] SAFETY SYRINGE AND METHOD OF USING SAME

[76] Inventor: Ricardo L. de la Fuente, 2415 Granada Blvd., Coral Gables, Fla. 33134

[21] Appl. No.: 679,753

[22] Filed: Apr. 3, 1991

[51] Int. Cl.$^5$ .............................................. A61M 5/32
[52] U.S. Cl. ................................. 604/198; 604/110; 604/187; 604/192; 604/199
[58] Field of Search ............... 604/110, 187, 192, 198, 604/199, 263, 227

[56] References Cited

U.S. PATENT DOCUMENTS

| | | |
|---|---|---|
| 2,571,653 | 10/1951 | Bastien . |
| 4,356,822 | 11/1982 | Winstead-Hall . |
| 4,425,120 | 1/1984 | Sampson et al. . |
| 4,610,667 | 9/1986 | Pedicano et al. . |
| 4,631,057 | 12/1986 | Mitchell . |
| 4,636,201 | 1/1987 | Ambrose et al. . |
| 4,664,259 | 5/1987 | Landis . |
| 4,723,943 | 2/1988 | Spencer . |
| 4,735,618 | 4/1988 | Hagen . |
| 4,738,663 | 4/1988 | Bogan . |
| 4,747,830 | 5/1988 | Gloyer et al. . |
| 4,747,837 | 5/1988 | Hauck . |
| 4,767,413 | 8/1988 | Haber et al. .................. 604/198 |
| 4,772,272 | 9/1988 | McFarland . |
| 4,790,827 | 12/1988 | Haber et al. . |
| 4,801,295 | 1/1989 | Spencer . |
| 4,842,587 | 6/1989 | Poncy . |
| 4,846,796 | 7/1989 | Carrell et al. . |
| 4,850,961 | 7/1989 | Wanderer et al. . |
| 4,850,994 | 7/1989 | Zerbst et al. . |
| 4,892,523 | 1/1990 | Haber et al. . |
| 4,898,590 | 2/1990 | Andors . |
| 4,900,311 | 2/1990 | Stern et al. . |
| 4,911,693 | 3/1990 | Paris .................................. 604/198 |
| 4,915,695 | 4/1990 | Koobs . |
| 4,915,696 | 4/1990 | Feimer . |
| 4,915,697 | 4/1990 | DuPont . |
| 4,915,698 | 4/1990 | Levenson . |
| 4,915,699 | 4/1990 | Kornberg . |
| 4,915,700 | 4/1990 | Noonan, Jr. . |
| 4,915,701 | 4/1990 | Halkyard . |
| 4,915,702 | 4/1990 | Haber . |
| 4,917,672 | 4/1990 | Terndrup et al. . |
| 4,917,673 | 4/1990 | Coplin . |
| 4,917,679 | 4/1990 | Kronner . |
| 4,969,877 | 11/1990 | Kornberg . |
| 4,973,316 | 11/1990 | Dysarz . |
| 4,973,317 | 11/1990 | Bobrove . |
| 4,973,318 | 11/1990 | Holm et al. . |
| 4,994,045 | 2/1991 | Ranford ............................... 604/263 |
| 5,013,302 | 5/1991 | Schmidt . |
| 5,019,043 | 5/1991 | Sequi Pastor et al. . |
| 5,019,044 | 5/1991 | Tsao . |
| 5,019,051 | 5/1991 | Hake ..................................... 604/263 |
| 5,057,079 | 10/1991 | Tiemann et al. ..................... 604/263 |
| 5,057,087 | 10/1991 | Harmon ................................ 604/198 |
| 5,059,185 | 10/1991 | Ryan .................................... 604/263 |

FOREIGN PATENT DOCUMENTS 0561841 10/1923 France ................................. 604/227

Primary Examiner—C. Fred Rosenbaum
Assistant Examiner—Ronald K. Stright, Jr.
Attorney, Agent, or Firm—Peter G. Dilworth; Rocco S. Barrese; Joseph J. Catanzaro

[57] ABSTRACT

A syringe is disclosed which includes a needle body having a proximal end and a distal end, a needle attached to the distal end of the needle body, a plunger for drawing fluid into the needle body through the needle, and a protective sheath configured and dimensioned to be positioned about the needle body and movable between a first distal position whereby the needle is shielded by the sheath and a proximal position whereby the needle is exposed. A system of slots and pegs is provided to releasably retain the protective sheath in the first distal position and to releasably retain the protective sheath in the proximal position. Also a system to retain and lock the protective sheath in a second distal position after use whereby the needle is protected by the sheath. A method of using the safety syringe to protect the needle from inadvertent contact with the user or any person in the area of use is also disclosed.

34 Claims, 7 Drawing Sheets

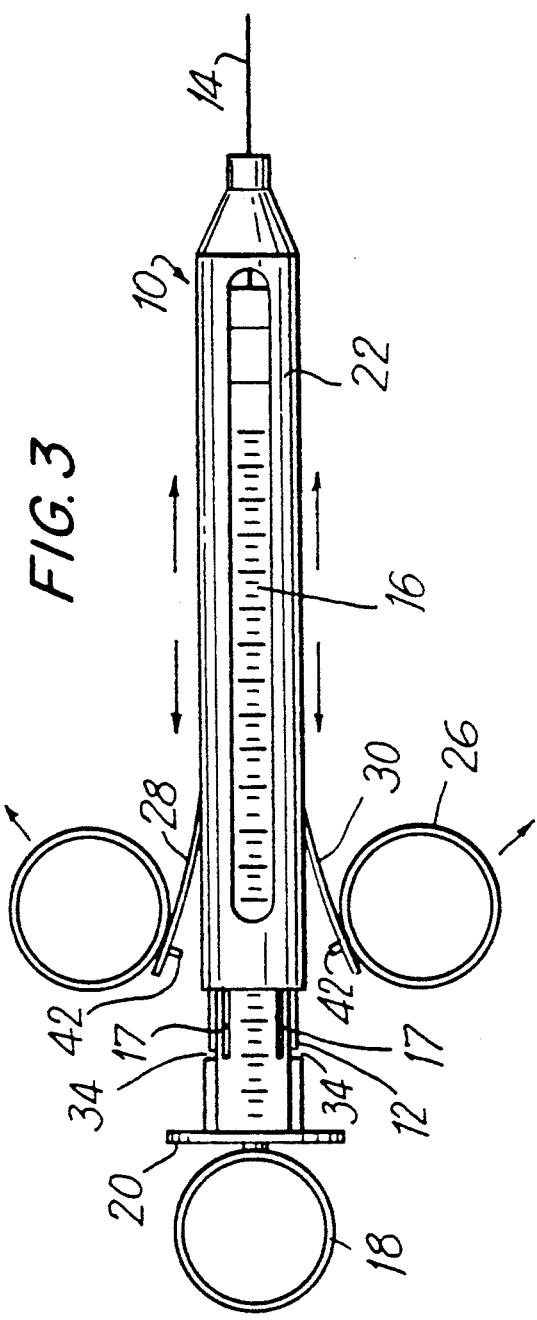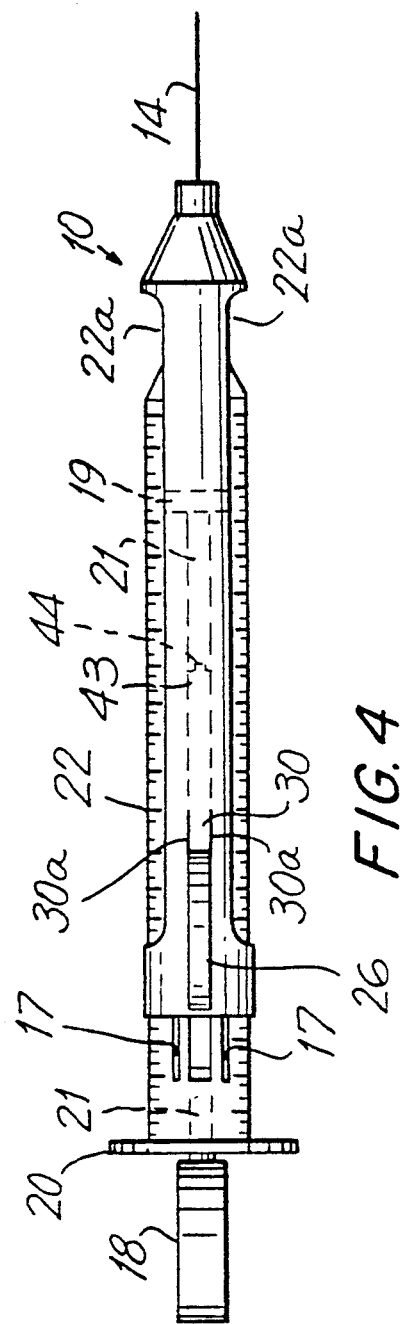

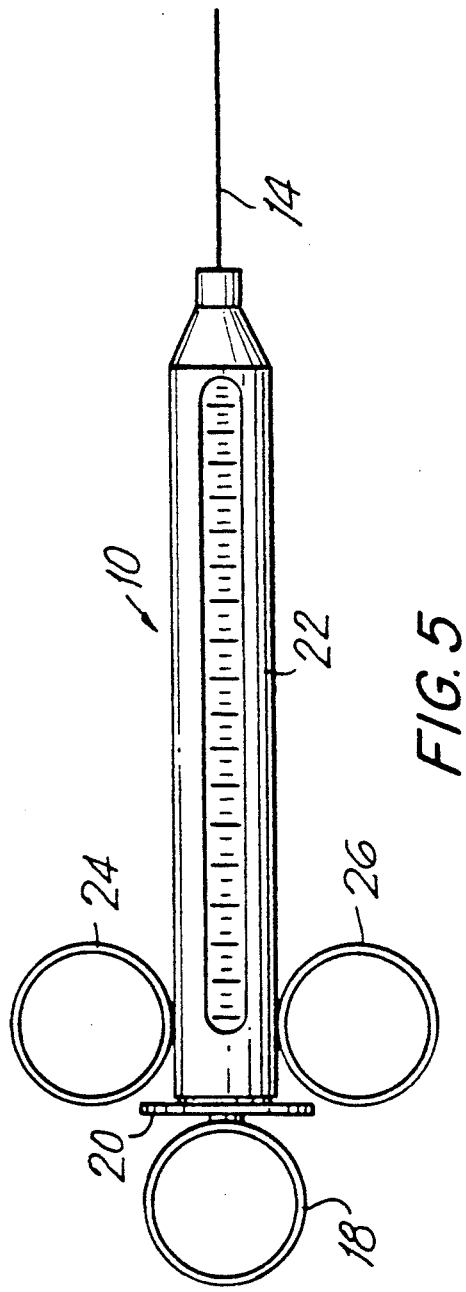
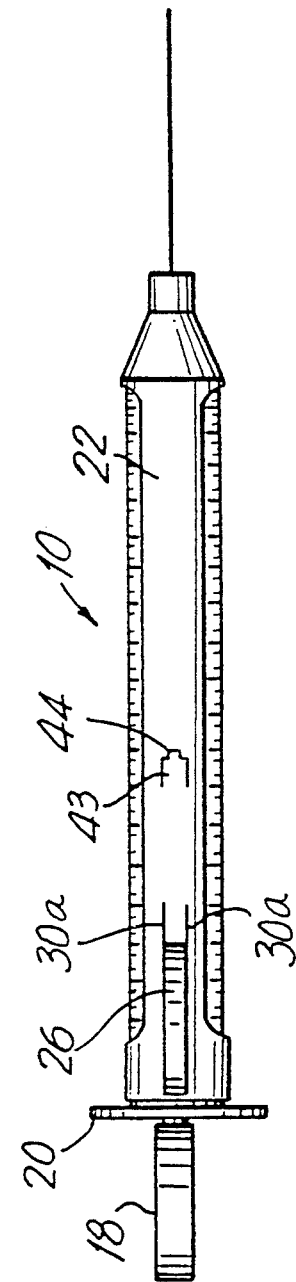

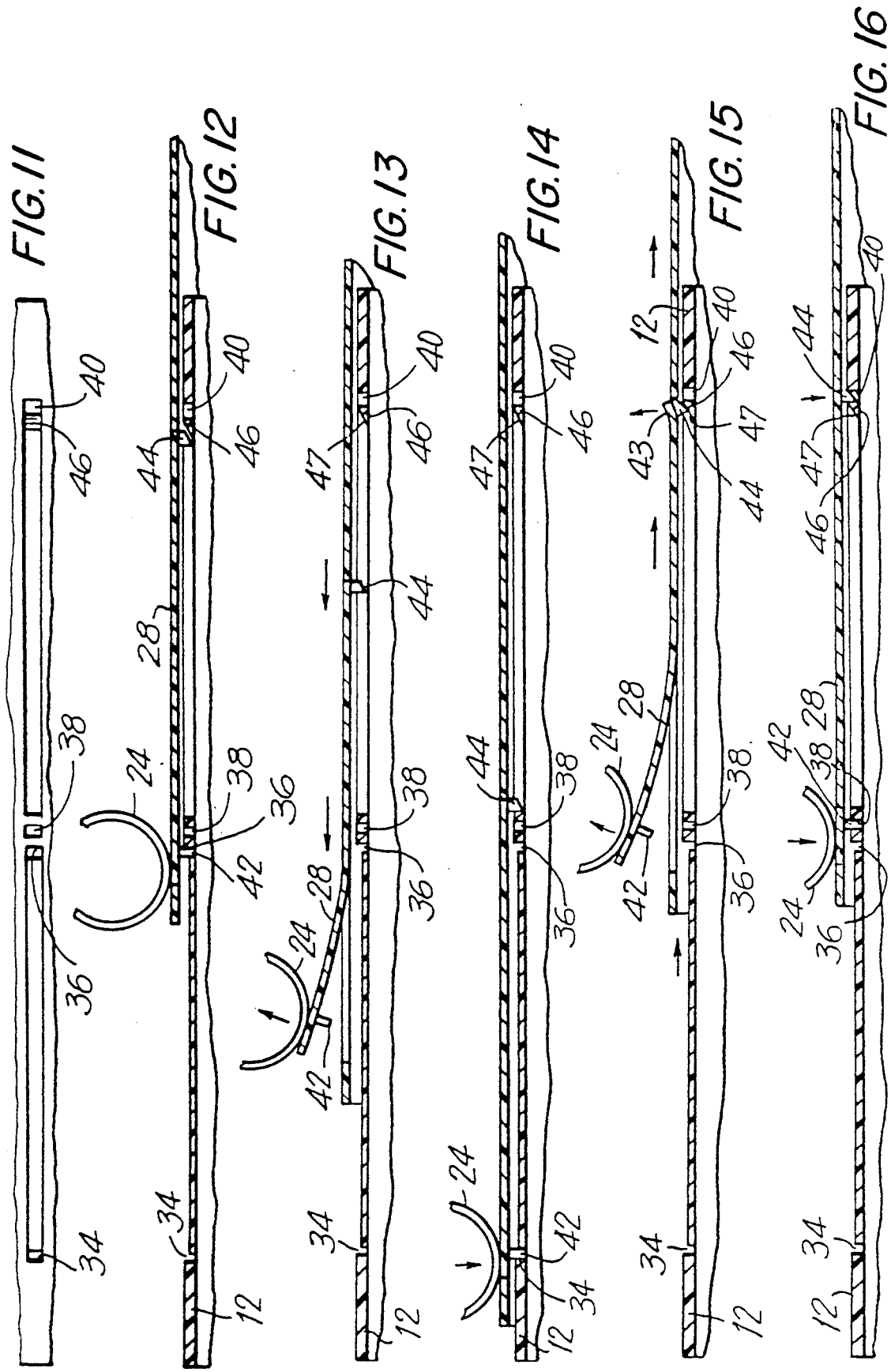

SAFETY SYRINGE AND METHOD OF USING SAME

CROSS REFERENCE TO RELATED DOCUMENTS

The present invention relates to a safety syringe as disclosed in Disclosure Document No. 245,403 filed Feb. 12, 1990.

BACKGROUND OF THE INVENTION

1. Field of the Invention

The present invention relates to a syringe. More particularly the syringe includes a safety sheath selectively movable by one hand to positions whereby the needle may be exposed or covered, one of the needle covering positions being automatically locked when the sheath is moved thereto.

2. Background of the Prior Art

Protection for medical personnel from inadvertent contact with contaminated syringe needles has become an increasing concern particularly because of the severity of certain infectious diseases which have developed. For example, the AIDS virus has been shown to be spread to persons who come into contact with a contaminated needle after the needle was used for a patient carrying the virus.

Numerous attempts have been made to protect medical personnel, patients and anyone in the area when syringes are used by providing various shielding devices for the needles. For example, U.S. Pat. No. 4,969,877 relates to a syringe which includes an outer casing into which the needle may be retracted after use. U.S. Pat. No. 4,973,316 relates to a one handed retractable sheath safety syringe. A number of other attempts at providing protection for safety syringe needles have been made.

None of the safety devices developed to date provide relatively simple and quick one hand application whereby the user may simply slide a protective device into several positions with one position being a locked position which is irreversible by normal action of the user. Further, there remains a need for such safety syringes which would be usable as an injecting syringe or as an aspirating syringe, all with one hand operation, while being simply automatically convertible to a configuration whereby the needle is covered and protected while preventing inadvertent re-exposure of the needle. The present invention provides such a safety syringe.

SUMMARY OF THE INVENTION

A syringe which comprises a needle body having a proximal end and a distal end, a needle attached to the distal end of the needle body, means for drawing fluid into the needle body through the needle, and a protective sheath configured and dimensioned to be positioned about the needle body and movable between a first distal position whereby the needle is shielded by the sheath and a proximal position whereby the needle is exposed. The syringe includes means to releasably retain the protective sheath in the first distal position, means to releasably retain the protective sheath in the proximal position, and means to retain the protective sheath in a second distal position after use whereby the needle is protected by the sheath. Preferably, the sheath automatically becomes locked in the second distal position when it is moved to this position.

In a preferred embodiment the needle body has a proximal end and a distal end and defines a fluid chamber. The needle is attached to the distal end of the body and communicates with the fluid chamber. Means is provided for manually drawing fluid into the chamber through the needle and the protective sheath is positioned about the needle body and movable between a first distal position whereby the needle is shielded by the sheath and a proximal position whereby the needle is exposed. Means to releasably retain the sheath in the first distal position is provided and means to releasably retain the protective sheath in the proximal position is provided. The syringe includes means to lockingly retain the protective sheath in a second distal position, the second distal position being distal of the first distal position whereby the needle is protected from unwanted contact after use.

Preferably the needle body is an elongated cylindrical member defining the inner fluid chamber and the fluid chamber is cylindrically shaped. A plunger assembly is positioned within the inner fluid chamber for drawing or expelling fluids with respect thereto. The needle body includes a plurality of slots dimensioned, positioned and configured for reception of correspondingly shaped pegs which extend inwardly of the protective sheath to retain the sheath in at least one of a plurality of selective positions relative to the needle body.

At least two of the slots in the needle body are positioned in the proximal portion of the needle body and are configured for reception of at least two correspondingly dimensioned pegs on the safety sheath to retain the safety sheath in the proximal position relative to the needle body whereby the needle is exposed for use. At least two of the slots are positioned in the distal portion of the needle body and are configured for reception of at least two correspondingly dimensioned pegs on the safety sheath to retain the safety sheath in the first distal position relative to the needle body, whereby the needle is covered. Further, at least two of the slots in the needle body are positioned distally of the first mentioned distal slots for reception of at least two of the pegs on the safety sheath, the pegs being dimensioned, positioned and configured to lockingly retain the safety sheath in the second distal position relative to the needle body.

The slots which retain the safety sheath in the second distal position are configured to retain the correspondingly configured and positioned locking pegs on the safety sheath in a manner whereby the locking pegs are not removable from the slots by normal action of the user. Further, the locking slots in the needle body are each positioned adjacent and distal of a ramped surface thereon, the ramped surface being adapted and configured for slidable reception of the locking pegs on the safety sheath to facilitate slidable entry of the locking pegs into the locking slots positioned distally of the ramped surfaces. The locking pegs on the safety sheath include a ramped surface substantially parallel to the ramped surface on the needle body to facilitate slidable engaged reception of the locking pegs into the locking slots.

In the safety syringe according to the invention, the locking pegs are attached to the safety sheath in a manner to be resiliently movable in a direction away from the needle body such that the pegs are resiliently biased in a direction toward the locking slots on the needle body to lock the position of the safety sheath in the second distal position. The ramped surface on the needle body extends in a direction radially outwardly of the needle body from the proximal end to the distal end of the ramped surface. The ramped surface on the peg attached to the safety sheath extends in a direction radially outward toward the inner surface of the safety sheath in a direction from the proximal end to the distal end of the ramped surface Further, the safety sheath is constructed of a resilient plastic material and the locking pegs are attached to strips formed integrally with the safety sheath and are adapted to be resiliently biased inwardly toward the safety sheath. The plastic material is transparent or translucent but may be opaque if desired. Such plastics as polyethylene polypropylene and polycarbonate are contemplated, but other suitable materials may be used.

The safety sheath includes two elongated strips attached to the safety sheath at their distal ends and resiliently biased inwardly toward the safety sheath. Also two similar locking strips are attached at their proximal ends and include the locking pegs.

Each elongated strip has an endless circular loop positioned at the proximal end, each loop being dimensioned for reception of one of the user's fingers. A plunger assembly is positioned within the needle body and adapted for drawing fluids therein through the needle by vacuum or out of the needle body by pressure. A finger loop is connected to the plunger assembly for movement of the plunger assembly in distal and proximal directions. The needle body includes at least one guide track extending along the length thereof and dimensioned for slidable reception of a correspondingly dimensioned peg extending inwardly of the inner surface of the safety sheath to retain the relative angular orientation between the safety sheath and the needle body. Preferably, at least four of the guide tracks are provided on the safety sheath and at least four of the correspondingly positioned and dimensioned pegs are provided. The tracks and the pegs are distributed approximately equally about the needle body to maintain rigidity and minimize lateral play within the safety sheath and the needle body. The elongated strips and the finger loops are integrally molded with the safety sheath in a manner which facilitates outward movement of the strips with respect to the safety sheath while the distal end of the strips are integrally attached to the safety sheath. The proximal ends of the locking strips are integrally molded with the safety sheath.

A method is disclosed for using a syringe having a hollow medical needle whereby the needle is protected from contact therewith before and after use, comprising providing a safety sheath in a first distal position whereby the needle is shielded prior to use, releasing the safety sheath and moving same to a proximal position whereby the needle is exposed for use, and advancing the safety sheath to a second distal position whereby the needle is protected by the safety sheath, the safety sheath having means to be locked into the second distal position whereby movement of the safety sheath to a position proximal thereof by the user is prevented.

According to the method the syringe includes an elongated needle body and the needle is attached to the distal end thereof, the needle communicating with an inner chamber defined by the needle body for reception of fluids through the needle and the sheath is automatically and simultaneously locked in the second distal position when advanced thereby by the user. The needle body includes a plunger assembly therein for drawing fluids into and discharging fluids out of the chamber.

BRIEF DESCRIPTION OF THE DRAWINGS

Preferred embodiments of the invention are described hereinbelow with reference to the drawings wherein:

FIG. 3 is a side view of the syringe shown in FIG. 1 with the safety sheath released and partially withdrawn to expose the needle;

FIG. 4 is a top view of the syringe shown in FIG. 3;

FIG. 5 is a side view of the safety syringe shown in FIG. 3 with the safety sheath in position in the fully withdrawn position to permit the syringe to be used normally;

FIG. 6 is top view of the safety syringe shown in FIG. 5;

FIG. 11 is a top view of the needle body with major portions removed, illustrating the relative positions of the slots in the needle body on one side which are associated with the safety locking system;

FIG. 12 is a side elevational view thereof, illustrating the safety locking system according to the invention with the relative positions between the safety sheath and the needle body shown in the initial position corresponding to FIG. 1;

FIG. 13 is a side cross-sectional view thereof, illustrating the relative positions of the safety sheath and needle body after the safety sheath has been partially withdrawn;

FIG. 14 is a side cross-sectional view thereof, illustrating the relative positions of the safety sheath and needle body in position for use of the syringe either as an injecting or a fluid aspirating syringe;

FIG. 15 is a side cross-sectional view thereof illustrating the relative positions of the safety sheath and needle body shown in FIG. 14 after use, with the safety sheath pushed distally to a position just prior to engagement of the safety locking system; and FIG. 16 is a side cross-sectional view thereof illustrating the needle body and the safety sheath with the safety sheath just distally of the position shown in FIGS. 1 and 2.

DETAILED DESCRIPTION OF THE PREFERRED EMBODIMENTS

In the description which follows "distal" means away from the user and "proximal" means toward the user.

Figure 1:
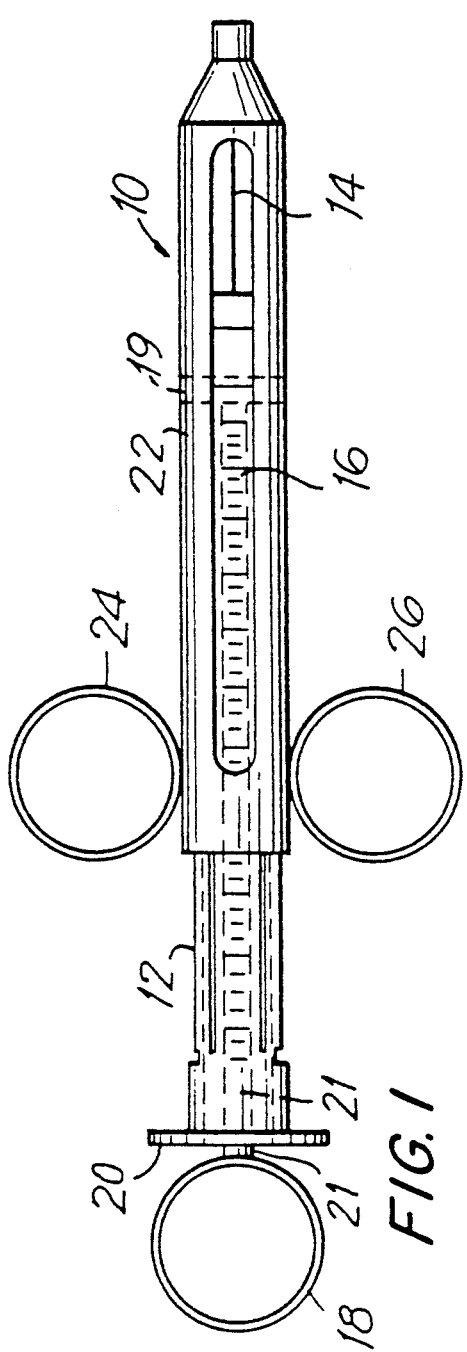
FIG. 1 is a side view of the safety syringe constructed according to the present invention with the safety sheath in the distal position protecting the needle from unintended contact.

Referring initially to FIG. 1 the safety syringe 10 constructed according to the present invention is shown. The syringe may be of the aspirating type or the injecting type. In the former, fluid is drawn from the body. In the latter, medication or other fluid is injected into the body by the needle. In either case, it is important to protect the needle after it has come in contact with the body fluids of the person in order to prevent inadvertent contact thereafter with a person other than the patient.

The safety syringe 10 includes a needle body 12 having a needle 14 at one end communicating with a chamber 16 defined internally of the needle body and shown in dotted lines. The needle is a medical or surgical type having a hollow cylindrical cross section for drawing and expelling liquids with respect to needle body 12. Finger loop 18 is attached to the needle body at a location just proximal of rear wall 20. A plunger 19 is shown schematically in dotted lines in FIGS. 1 and 4 and is connected to finger loop 18 by elongated member 21, also shown schematically.

Figure 2:
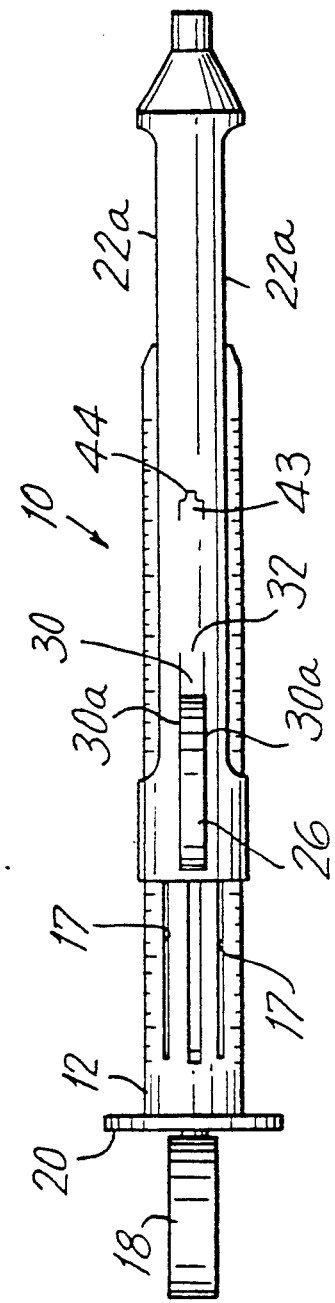
FIG. 2 is a top view of the safety syringe shown in FIG. 1.

As shown in FIG. 1, safety sheath 22 includes two finger loops 24, 26 attached to the sheath via relatively thin strips which are preferably formed of resilient material integrally with sheath 22 and which bias the loops inwardly toward the body to the position shown in FIG. 1. Preferably the safety sheath 22 is constructed of a transparent or translucent resilient plastic material and formed as a cylindrical tubular member having resilient strips 28, 30 which are separable from the body of the safety sheath and are attached at the distalmost portion shown at 32. Although the strips are integrally molded, i.e., monolithic with the safety sheath, they are actually separated from the main sheath by molded "cuts" shown at 30a in FIG. 2, which define the strips and permit the strips to be moved manually toward and away from the sheath. Further, as seen in FIGS. 1 and 2, the safety sheath is generally cylindrical and has portions of the cylindrical wall eliminated as shown at 22a to permit viewing of the transparent liquid measure 16 of the needle body. Such plastic materials as polyethylene, polypropylene, or polycarbonates such as LEXAN brand material marketed by General Electric Company, Pittsfield, Mass., are contemplated. As noted, preferably, the sheath and the body are integrally molded as shown from such plastic materials.

The sheath 22 is dimensioned and configured to slide between proximal and distal positions relative to body 16. Four tracks in the form of elongated slots 17 are formed in body 12 and four corresponding pegs 15 extend inwardly from the inner wall of the sheath 22 and are slidably positioned within tracks 17 to retain the relative angular orientation of sheath 22 with respect to body 12. In FIGS. 1 and 2 only two of such tracks 17 are shown. The normal pre-use condition of the syringe is as shown in FIG. 1.

In FIGS. 3 and 4 the body 12 is shown after the safety sheath 22 has been partially withdrawn proximally by the user by placing the index and middle finger into the finger loops 26, 24 and separating the loops as shown to release pegs 42 from peg reception notches 36 shown in FIG. 11. During this motion the user's thumb is positioned within finger loop 18. The safety sheath 22 is withdrawn fully to the proximalmost position shown in FIGS. 5 and 6 when finger loops 24, 26 are permitted to return to their inwardly biased positions. At this time, pegs 42 enter slots 34 and thereby fix the position of the safety sheath 22 relative to the body 12 in the needle exposed condition shown in FIGS. 5 and 6.

Figure 7:
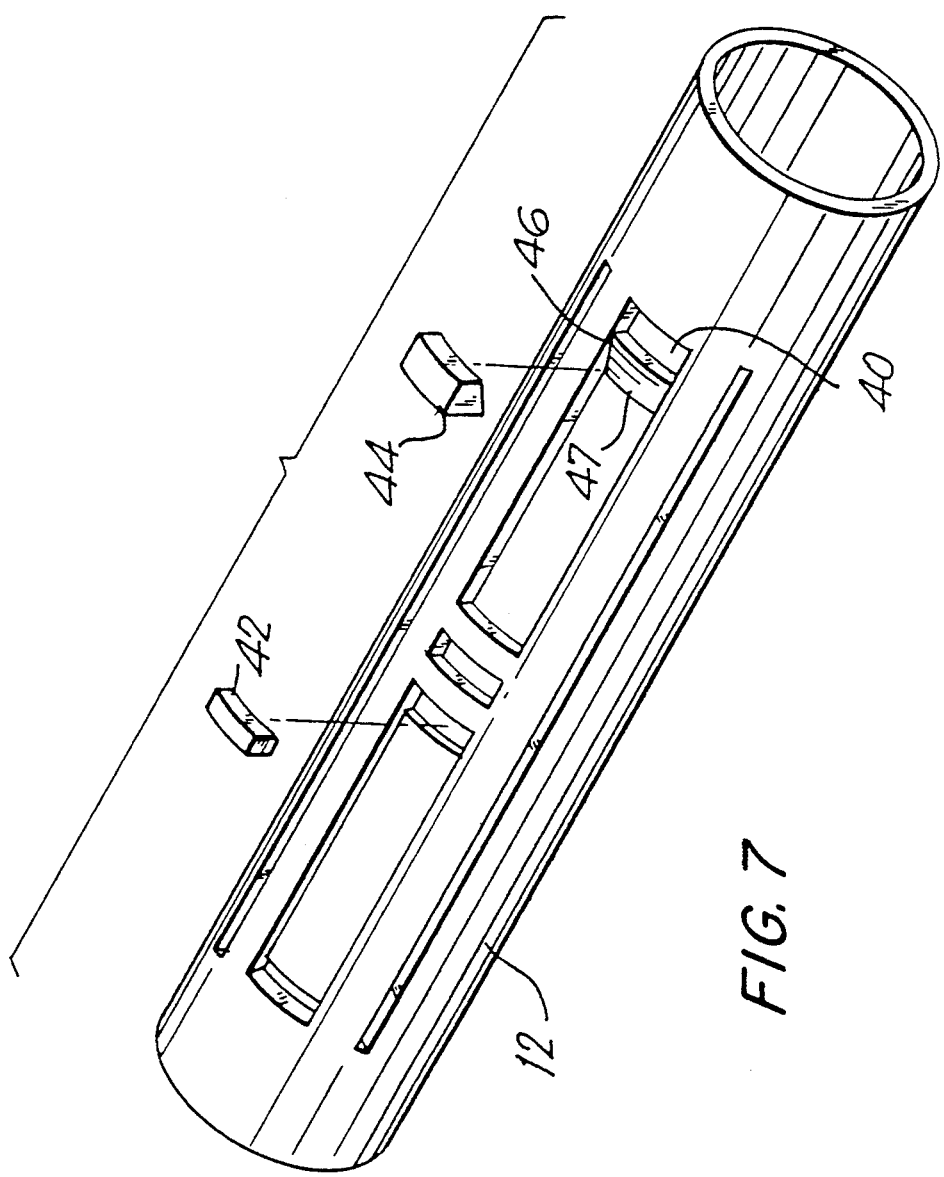
FIG. 7 is a perspective view with parts removed, illustrating schematically, one side of the body of the syringe constructed according to the present invention and the locking system for the safety syringe.
Figure 8:
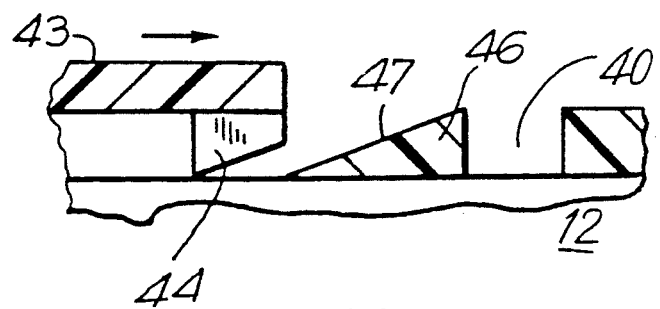
FIG. 8 is a greatly enlarged cross-sectional view illustrating the sheath safety locking mechanism as the safety sheath is being moved distally after using the syringe.
Figure 9:
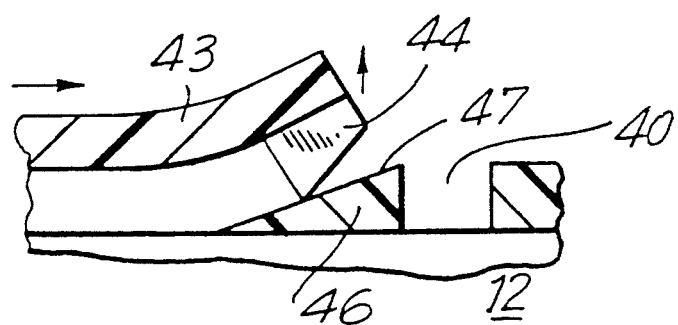
FIG. 9 is a greatly enlarged cross-sectional view of the safety locking mechanism shown in FIG. 8 just prior to locking the safety sheath in the protective position over the needle.

The system for releasably retaining the safety sheath 22 in the pre-use condition and the final safety locking system will now be described in connection with FIGS. 7, 8 and 11-16. In connection therewith for convenience of illustration in FIGS. 11-16 the locking system associated with one finger ring 24 will be described. In FIG. 7, the finger rings 26 and 24 and the remaining portions of the needle body 12 and sheath 22 have been removed for illustration purposes. As constructed, the locking system for the other finger ring 26 is identical but opposite in configuration and position to the system associated with the finger ring 24.

Body 12 includes a series of slots 34, 36, 38, 40 as shown in FIG. 11. Beneath finger ring 24 is positioned peg 42 adapted to enter into either of slots 34, 36 or 38 to establish the position of the safety sheath 22 relative to the body 12. Third, or locking peg 44 is positioned on the internal wall of the sheath 22 and is configured to enter the distal slot 40 of the needle body. Locking peg 44 is attached to strip 43 which is cut out of the safety sheath 22 such that the peg 44 is resiliently biased toward the body 12 by the inward bias of strips 28, 30. This bias is due to the natural resilience of the plastic material forming the sheath 22 from which the sheath 22 and strips 28, 30 are integrally molded. Just proximal of the distal slot 40 is a ramped member 46 for slidable contact by locking peg 44 and reception of peg 44 into slot 40 to lock and fix the position of the sheath in the distalmost, or needle protective position.

In operation, the safety syringe functions as follows. The syringe is delivered to the user in the configuration shown in FIG. 1 with the safety sheath 22 in the distal position corresponding to peg 44 being positioned as shown in FIG. 12 while peg 42 immediately beneath ring 24 being positioned within slot 36. Distal or proximal movement of sheath 22 is thus prevented by the position of peg 42 within slot 36.

To retract the sheath the user positions the thumb within finger loop 18 and the index and middle fingers respectively in one of the aspirating loops 24, 26 as described previously. Thereafter, the index finger and middle finger are separated in opposite directions to release pegs 42 from slots 36 as shown in FIGS. 3, 4 and 13. The finger motion which releases the pegs is opposite the inward natural resilient force provided by strips 28, 30 as shown in FIG. 3, which are formed out of sheath 22 and are resiliently biased toward the body 12. The configuration of body 12 is shown clearly in FIG. 7. The side not shown is the same. As will be observed from the drawings, after the pegs 42 are released the sheath is now free to travel in a proximal direction to expose the needle.

Upon withdrawing the sheath proximally to the position shown in FIG. 14 finger loops 24, 26 are returned to the normal inward positions and pegs 42 re-enter the rearwardly positioned slots 34 thereby fixing the position of sheath 22 with respect to body 12 and exposing needle 14 for use. At this point, the needle may be inserted into the patient's body and the thumb ring 18 may be withdrawn to withdraw the internal plunger assembly 19 of the needle body for normal use of the syringe as an aspirating device, i.e. to draw fluid from the body. Alternatively, this motion may be used to draw fluid from a separate source—such as medication vial—for injection into the body as shown in FIG. 12. When the syringe is in the normal use condition with pegs 42 within slots 34, the distal locking pegs 44 are in a position just distal of slot 38 as shown in FIG. 14.

Figure 10:
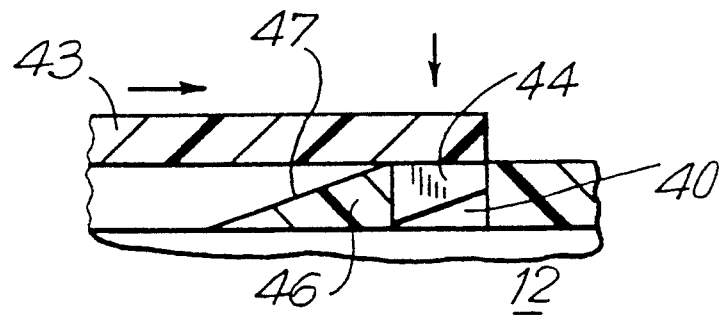
FIG. 10 is a greatly enlarged cross-sectional view of the safety locking mechanism shown in FIGS. 8 and 9 when the safety sheath has been moved distally to the needle protective distalmost position preventing further needle use.
Figure 17:
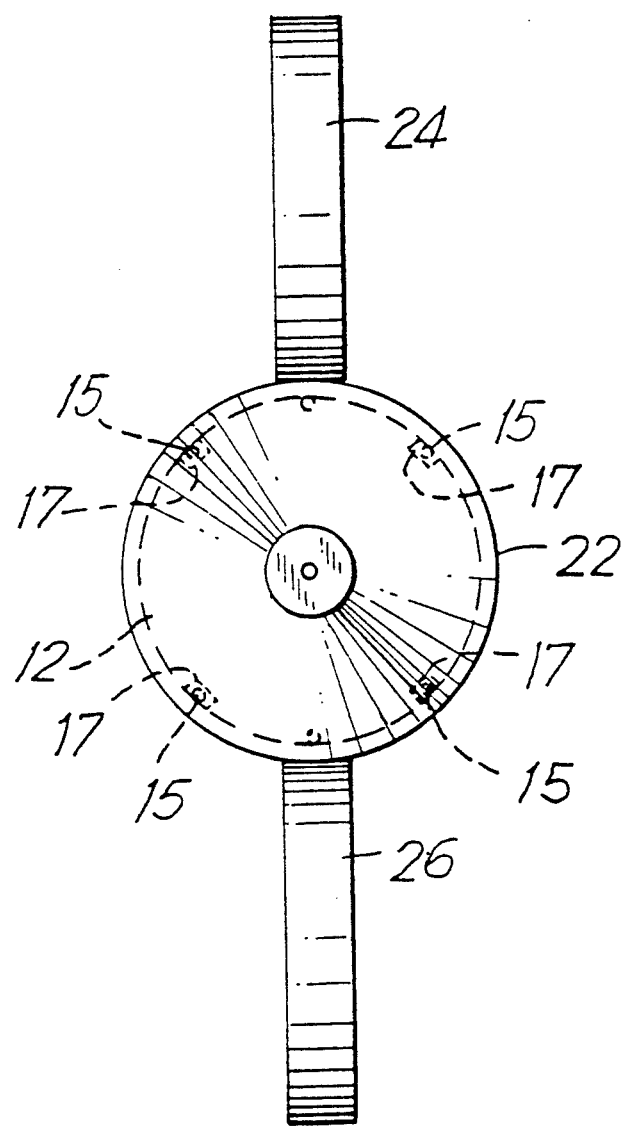
FIG. 17 is a proximal end view of the safety syringe shown in FIG. 5 with the rear wall and thumb ring removed.

After normal use of the syringe the aspirating finger loops 24, 26 are once again separated laterally by the index and middle fingers to release pegs 42 from the proximal slots 34 freeing the sheath for distal movement to a distal position covering needle 14 and corresponding to the position of peg 44 within slot 40 as shown in FIG. 10. During this movement, peg 44, which is ramped oppositely— and preferably approximately parallel—to ramp 46 as shown, slides over ramp surface 47 of ramp 46 and drops into slots 40 under the natural inward resilient bias provided by the resilient material of strip 43. Resilient strips 43 are preferably integrally molded with sheath 22 similarly to strips 28, 30. They are essentially separated from sheath 22 by cuts 43a and in the same manner as strips 28, 30 to bias pegs 44 inwardly toward body 12. When the pegs 44 are positioned within slots 40 the proximal pegs 42 will be positioned within slots 38, the positions of which are just distal of the initial slots 36. As noted, since the pegs 44 are also positioned within slots 40 which are located just distally of the initial position of pegs 44 shown in FIG. 12, the distal position of sheath 22 will be fixed relative to the body 12.

It will be appreciated from the view shown in FIGS. 10 and 16 of the pegs 44 within slots 40 that the configuration of the pegs 44 are such that sheath 22 is locked into a distal needle protective position just slightly distal of the initial position shown in FIG. 1. The resilient action of the material of the strips 43 which cause pegs 44 to become locked within slots 40 render the sheath 22 immovable under normal use by the user. Withdrawal of safety sheath 22 from this locked position is virtually impossible forcing pegs 44 outwardly of slots 40 against the inward resilient force of strips 43. In any event, normal user motions will not release the safety sheath. Thus, the needle is protected by the position of the sheath and inadvertent contact with the known user or other party is virtually impossible without forcing the pegs 44 out of slots 40 or physically destroying the safety sheath 22.

Other variations of the present invention will become evident to persons skilled in the art within the scope of the claims appended hereto.

What is claimed is:

1. A safety syringe which comprises:
   a) a needle body having a proximal end and a distal end and defining a fluid chamber;
   b) a needle attached to said distal end of said body and communicating with said fluid chamber;
   c) means for manually drawing fluid into said chamber and expelling fluids out of said chamber through said needle;
   d) a safety sheath positioned about said needle body, said sheath having a fixed angular orientation with respect to said needle body about a longitudinal axis extending therethrough, and movable between a first distal position whereby said needle is shielded by said sheath, a proximal position whereby said needle is exposed, and a second distal position whereby said needle is protected by said sheath;
   e) means movable toward and away from said safety sheath to releasably retain said sheath in said first distal position and said proximal position and including means for facilitating reception of a user's finger; and
   f) means to lockingly retain said safety sheath in said second distal position, said second distal position being distal of said first distal position whereby said needle is protected from unwanted contact after use.

2. A safety syringe according to claim 1 wherein said needle body is an elongated member defining said inner fluid chamber.

3. A safety syringe according to claim 2 wherein said needle body is an elongated cylindrical member and said inner fluid chamber is cylindrically shaped, and a plunger assembly is positioned within said inner fluid chamber for drawing or expelling fluids with respect thereto.

4. A safety syringe according to claim 3 wherein said needle body includes a plurality of slots dimensioned, positioned and configured for reception of a plurality of corresponding locking pegs which extend inwardly of said safety sheath to retain said sheath in at least one of a plurality of selective positions relative to said needle body.

5. A safety syringe according to claim 4 wherein at least two of said plurality of slots in said needle body are positioned in the proximal portion of said needle body and are configured for reception of at least two of said plurality of locking pegs on said safety sheath to retain said safety sheath in said proximal position relative to said needle body whereby said needle is exposed for use.

6. A safety syringe according to claim 5 wherein at least two of said plurality of slots are positioned in the distal portion of said needle body and are configured for reception of at least two of said plurality of locking pegs on said safety sheath to retain said safety sheath in said first distal position relative to said needle body, whereby said needle is covered.

7. A safety syringe according to claim 6 wherein at least two of said plurality of slots in said needle body are positioned distally of said first mentioned distal slots for reception of at least two of said plurality of locking pegs on said safety sheath, said pegs being dimensioned, positioned and configured to lockingly retain said safety sheath in said second distal position relative to said needle body.

8. A safety syringe according to claim 7 wherein said slots to retain said safety sheath in said second distal position are configured to retain said correspondingly configured and positioned locking pegs on said safety sheath in a manner whereby said locking pegs are not removable from said slots by normal action of the user.

9. A safety syringe according to claim 8 wherein said locking slots in said needle body are each positioned adjacent and distal of a ramped surface thereon, said ramped surface being adapted and configured for slidable reception of said locking pegs on said safety sheath to facilitate slidable entry of said locking pegs into said locking slots positioned distally of said ramped surfaces.

10. A safety syringe according to claim 9 wherein said locking pegs on said safety sheath include a ramped surface substantially parallel to said ramped surface on said needle body to facilitate slidable engaged reception of said locking pegs into said locking slots.

11. A safety syringe according to claim 10 wherein said locking pegs are attached to said safety sheath in a manner to be resiliently movable in a direction away from said needle body such that said locking pegs are resiliently biased in a direction toward said slots on said needle body to lock said safety sheath in said second distal position.

12. A safety syringe according to claim 11 wherein said ramped surface on said needle body extends in a direction radially outwardly of said needle body from the proximal end to the distal end of said ramped surface.

13. A safety syringe according to claim 12 wherein said ramped surface on each of said locking pegs attached to said safety sheath extends in a direction radially outwardly toward the inner surface of said safety sheath in a direction from the proximal end to the distal end of said ramped surface.

14. A safety syringe according to claim 13 wherein said safety sheath is constructed of a resilient material and said locking pegs are attached to strips formed integrally with said safety sheath and are adapted to be resiliently biased inwardly toward said safety sheath.

15. A safety syringe according to claim 14 wherein said resilient material is plastic.

16. A safety syringe according to claim 15 wherein said plastic is transparent or translucent.

17. A safety syringe according to claim 16 wherein said plastic is at least one of polyethylene polypropylene and polycarbonate.

18. A safety syringe according to claim 17 wherein said safety sheath includes at least two elongated strips formed therefrom and attached at their distal ends to said safety sheath intermediate the length thereof and the proximal ends of said strips resiliently biased inwardly toward said safety sheath.

19. A safety syringe according to claim 18 wherein each of said elongated strips have a continuous loop structure positioned at the proximal end thereof, each loop dimensioned for reception of one of the user's finger.

20. A safety syringe according to claim 19 wherein each finger loop is circular.

21. A safety syringe according to claim 20 wherein a finger loop is connected to said plunger assembly for movement of said plunger assembly in distal and proximal directions.

22. A safety syringe according to claim 21 wherein said elongated strips and said finger loops are integrally molded with said safety sheath in a manner which facilitates outward movement of said strips with respect to said safety sheath while the distal end of said strips are integrally attached to said safety sheath.

23. A safety syringe according to claim 1 wherein said needle body includes at least one guide track extending lengthwise thereof and dimensioned for slidable reception of at least one correspondingly positioned and dimensioned guide peg extending inwardly of the inner surface of said safety sheath to retain the relative angular orientation between said safety sheath and said needle body.

24. A safety syringe according to claim 1 wherein said needle body includes at least four guide tracks extending lengthwise thereof and said safety sheath includes at least four correspondingly positioned and dimensioned guide pegs, said tracks and said pegs being distributed approximately equally about said needle body to maintain rigidity and minimize lateral play within said safety sheath and said needle body.

25. A safety syringe according to claim 1 wherein said needle body comprises at least two guide tracks extending lengthwise thereof and dimensioned for slidable reception of at least two correspondingly positioned and dimensioned guide pegs extending inwardly of the inner surface of said safety sheath to retain the relative angular orientation between said safety sheath and said needle body.

26. A safety syringe according to claim 1 wherein said needle body comprises at least two guide tracks extending lengthwise thereof and dimensioned for slidable reception of at least four correspondingly positioned and dimensioned guide pegs extending inwardly of the inner surface of said safety sheath to retain the relative angular orientation between said safety sheath and said needle body.

27. A safety syringe according to claim 1 wherein said needle body comprises at least three guide tracks extending lengthwise thereof and dimensioned for slidable reception of at least three correspondingly positioned and dimensioned guide pegs extending inwardly of the inner surface of said safety sheath to retain the relative angular orientation between said safety sheath and said needle body.

28. In combination with a syringe having a needle body having a generally cylindrical hollow needle attached to a distal end thereof and having means for drawing fluid into or expelling fluid out of a chamber defined internally of said needle body, the improvement in combination therewith which comprises a safety sheath positioned about said needle body, said sheath having a fixed angular orientation with respect to said needle body about a longitudinal axis extending therethrough, and adapted for slidable movement between a first distal position, a second distal position and a proximal position relative to said needle body, means movable toward and away from said sheath and releasably engagable with said needle body to releasably retain said safety sheath in said first distal position whereby said needle is covered by said safety sheath and said proximal position whereby said needle is exposed for use, and including means for facilitating reception of a user's finger at least one guide track extending lengthwise of said needle body and at least one correspondingly positioned and dimensioned guide peg extending inwardly of said sheath for cooperating with said guide tracks to maintain the angular orientation of said sheath with respect to said needle body while permitting relative distal and proximal movement therebetween, and means to lockingly retain said safety sheath in said second distal position whereby said needle is protected thereby, said last mentioned retaining means being substantially locked from disengagement by the user.

29. A syringe according to claim 28 wherein said needle body comprises at least two of said guide tracks and said safety sheath comprises at least two of said correspondingly positioned and dimensioned guide pegs.

30. A syringe which comprises:
a) a needle body having a proximal end and a distal end;
b) a needle attached to said distal end of said needle body;
c) means for drawing fluid into said needle body and expelling fluid out of said needle body through said needle;

d) a protective sheath configured and dimensioned to be positioned about said needle body, said sheath having a fixed angular orientation with respect to said needle body about a longitudinal axis extending therethrough, and movable between a first distal position whereby said needle is shielded by said sheath, a proximal position whereby said needle is exposed, and a second distal position distal of said first distal position whereby said needle is protected from unwanted contact after use;

e) means movable toward and away from said protective sheath to releasably retain said protective sheath in said first distal position and said proximal position and including means for facilitating reception of a user's finger; and f) means to lockingly retain said protective sheath in said second distal position after use whereby said needle is protected by said sheath.

31. A syringe which comprises:

a) a cylindrical needle body having a proximal end and a distal end, said needle body including a plurality of slots;

b) a needle attached to said distal end of said needle body;

c) a plunger assembly for drawing fluid into said needle body and expelling fluid out of said needle body; and d) a protective sheath configured and dimensioned to be positioned about said needle body and movable between a first distal position wherein said needle is shielded by said sheath and a proximal position wherein said needle is exposed, said sheath including a plurality of resilient strips formed therefrom, at least two of said strips including at least one peg extending inwardly therefrom to cooperate with said plurality of slots of said needle body to retain said sheath in a plurality of axial positions relative to said needle body, said strips being movable toward and away from said sheath to thereby allow selective contact between said pegs on said strips and said slots of said needle body, at least two of said strips having a continuous loop positioned at a proximal end portion thereof for reception of the user's finger, whereby said protective sheath may be withdrawn from said first distal position to said proximal position to permit use of said needle, and thereafter advanced to a second distal position wherein said protective sheath is locked in a needle protective position by reception of at least two of said locking pegs with at least two of said slots.

32. A method of using a syringe having a hollow medical needle whereby the needle is protected from user contact before and after use, comprising:

a) providing a needle body having a proximal end and a distal end and having said needle attached thereto, a safety sheath having a fixed angular orientation with respect to said needle body about a longitudinal axis extending therethrough, means movable toward and away from said sheath and releasably engageable with said needle body for releasably retaining said sheath in a first distal position whereby said needle is shielded prior to use and a proximal position whereby said needle is exposed for use, and including means for facilitating reception of a user's finger and means to lockingly retain said sheath in a second distal position distal of said first distal position whereby said needle is shielded by said sheath;

b) moving said movable means away from said safety sheath to thereby release said safety sheath from said first distal position and moving said safety sheath to said proximal position whereby said needle is exposed for use; and c) advancing said safety sheath to said second distal position whereby said needle is protected by said safety sheath and contact therewith by the user is prevented.

33. A method of using a syringe according to claim 32 whereby said syringe includes an elongated needle body and said needle is attached to the distal end thereof, said needle communicating with an inner chamber defined by said needle body for reception of fluids through said needle and said sheath is automatically and simultaneously locked in said second distal position when advanced thereby by the user.

34. A method of using a syringe according to claim 29 wherein said needle body includes a plunger assembly therein for drawing fluids into and discharging fluids out of said chamber.

* * * * *